(12) United States Patent
Czaplewski et al.

(10) Patent No.: US 10,017,610 B2
(45) Date of Patent: Jul. 10, 2018

(54) SILICONE-BASED THERMAL INTERFACE MATERIALS

(71) Applicant: International Business Machines Corporation, Armonk, NY (US)

(72) Inventors: Sarah K. Czaplewski, Rochester, MN (US); Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/426,157

(22) Filed: Feb. 7, 2017

(65) Prior Publication Data

US 2017/0145163 A1    May 25, 2017

Related U.S. Application Data

(62) Division of application No. 14/856,134, filed on Sep. 16, 2015.

(51) Int. Cl.
| | | |
|---|---|---|
| *C08G 77/38* | (2006.01) | |
| *H01L 23/373* | (2006.01) | |
| *C07F 7/08* | (2006.01) | |
| *C07F 7/18* | (2006.01) | |

(52) U.S. Cl.
CPC .............. *C08G 77/38* (2013.01); *C07F 7/081* (2013.01); *C07F 7/18* (2013.01); *H01L 23/3737* (2013.01)

(58) Field of Classification Search
USPC .................................................. 528/10–43
See application file for complete search history.

(56) References Cited

U.S. PATENT DOCUMENTS

| | | |
|---|---|---|
| 6,126,865 A | 10/2000 | Haak et al. |
| 6,764,759 B2 | 7/2004 | Duvall et al. |
| 7,014,889 B2 | 3/2006 | Groves et al. |
| 2003/0064248 A1 | 4/2003 | Wolk et al. |
| 2005/0222323 A1 | 10/2005 | Zhou et al. |
| 2008/0166552 A1 | 7/2008 | Cloud et al. |
| 2008/0318057 A1 | 12/2008 | Sherman et al. |
| 2008/0318058 A1 | 12/2008 | Sherman et al. |
| 2010/0226701 A1 | 9/2010 | Moorlag |
| 2010/0280148 A1 | 11/2010 | Webster et al. |
| 2011/0071270 A1 | 3/2011 | Hays et al. |
| 2011/0265979 A1 | 11/2011 | Chen et al. |
| 2012/0125436 A1 | 5/2012 | Cummings et al. |
| 2012/0171915 A1 | 7/2012 | Bartholomew et al. |
| 2013/0280912 A1* | 10/2013 | Ogihara ................ C07F 7/1836 438/694 |

FOREIGN PATENT DOCUMENTS

JP         5-39358       *   2/1993

OTHER PUBLICATIONS

"List of IBM Patents or Patent Applications Treated as Related".
US Patent Application entitled "Silicone-Based Thermal Interface Materials", U.S. Appl. No. 14/856,134, filed Sep. 16, 2015.

* cited by examiner

*Primary Examiner* — Marc S Zimmer
(74) *Attorney, Agent, or Firm* — Patterson + Sheridan, LLP

(57) ABSTRACT

In an example, a silicone-based thermal interface material includes a thermally conductive material and a silicone-based polymeric material having a solubility parameter that is not less than 9.09 $cal^{1/2}$ $cm^{-3/2}$.

5 Claims, 3 Drawing Sheets

SILICONE-BASED THERMAL INTERFACE MATERIALS

CROSS-REFERENCE TO RELATED APPLICATIONS

This application is a divisional of co-pending U.S. patent application Ser. No. 14/856,134, filed Sep. 16, 2015 and entitled "SILICONE-BASED THERMAL INTERFACE MATERIALS", which is herein incorporated by reference in its entirety.

FIELD OF THE DISCLOSURE

The present disclosure relates generally to silicone-based thermal interface materials.

BACKGROUND

Oil immersion cooling is the submersion of information technology hardware into an oil in order to thermally cool the hardware during operation. Compared to air cooling, immersion cooling offers several advantages, such as reduced power consumption, lower cost, increased rack density, improved board performance, reduction of failures/overheating/hot spots, limited infrastructure, flexibility, and reduced costs of enclosures. With the move to these types of cooling systems, materials compatibility becomes challenging as some materials may degrade or swell within the oil coolant.

SUMMARY OF THE DISCLOSURE

According to an embodiment, a silicone-based thermal interface material is disclosed. The silicone-based thermal interface material may include a thermally conductive material and a silicone-based polymeric material. The silicone-based polymeric material may have a solubility parameter that is not less than 9.09 $cal^{1/2}$ $cm^{-3/2}$.

According to another embodiment, a process for the production of a silicone-based polymeric material is disclosed. The process may include chemically reacting a protecting group with a brominated alcohol to form a protected brominated alcohol. The process may include chemically reacting the protected brominated alcohol with an alkoxysilane to form a protected alcohol silane. The process may also include forming a mixture of the protected alcohol silane and a polyorganosiloxane to form a protected alcohol silane, and the mixture may be polymerized to form a grafted polyorganosiloxane. The process may further include chemically reacting a deprotecting group with the grafted polyorganosiloxane to generate a silicone-based polymeric material having a solubility parameter that is not less than 9.09 $cal^{1/2}$ $cm^{-3/2}$.

According to another embodiment, an apparatus is disclosed. The apparatus may include a first component representing a heat source, a second component, and a silicone-based thermal interface material disposed between the first component and the second component. The silicone-based thermal interface material includes a thermally conductive material and a silicone-based polymeric material. The silicone-based polymeric material may have a solubility parameter that is not less than 9.09 $cal^{1/2}$ $cm^{-3/2}$.

One advantage of the present disclosure is the ability to utilize a silicone-based thermal interface material in an immersion cooling environment (e.g., where mineral oil is used as an immersion cooling fluid). Shifting the solubility parameter of a silicone-based material away from the solubility parameter of an immersion cooling fluid may reduce/prevent swelling and associated heat transfer performance degradation that may be associated with use of some silicone-based thermal interface materials that are designed for use in an air cooled environment.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

Figure 1:
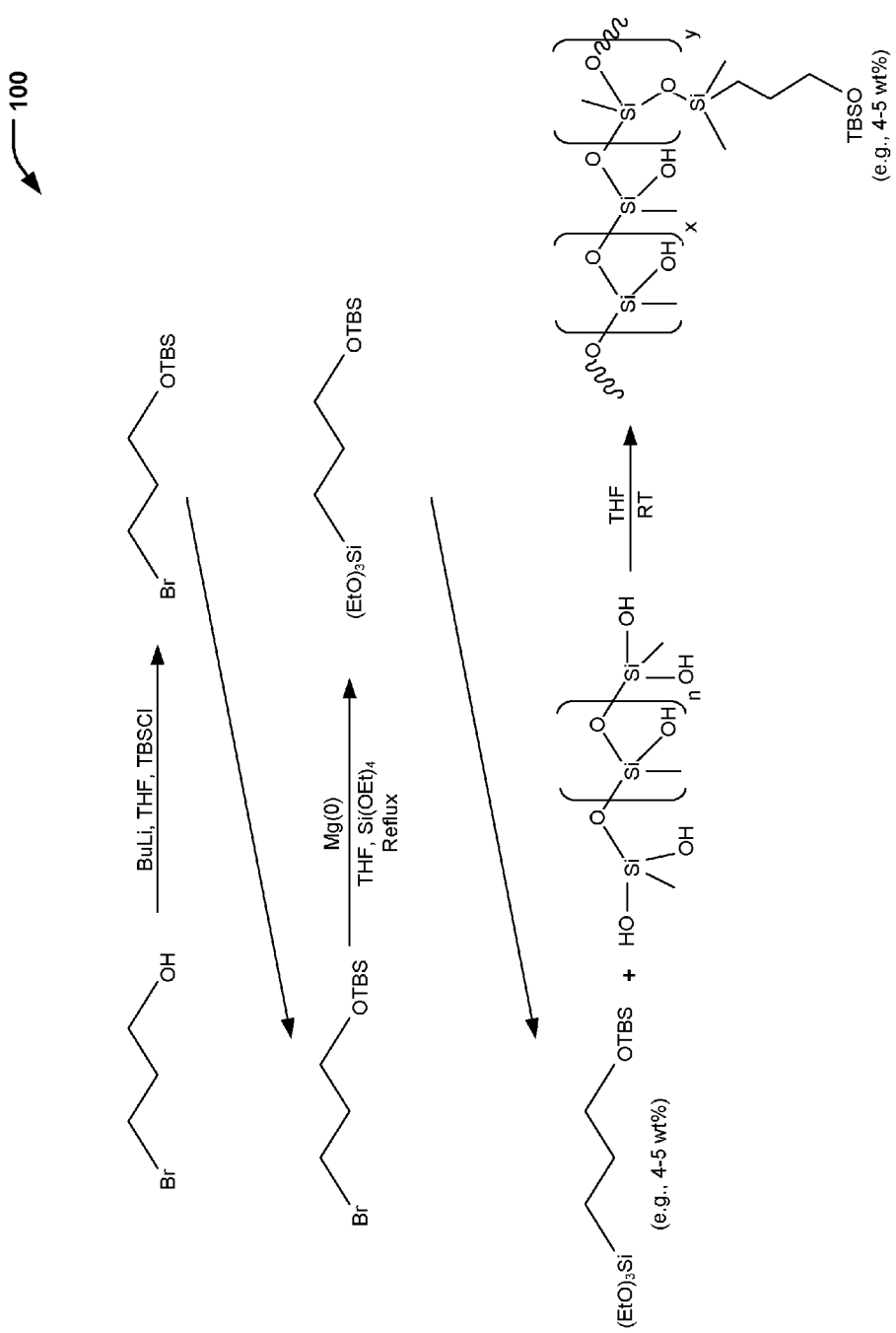
FIG. 1 is a chemical reaction diagram showing the preparation of a functionalized silicone-based material (in protected form), according to an embodiment.

This application is about performing reactions using hydroxyl-terminated polyorganosiloxane (silicone) polymers having one or more pendant hydroxyl groups to form grafted polyorganosiloxane polymers. In this application, where reference is made to a polyorganosiloxane, and in particular to polydimethylsiloxane (PDMS), reacting with an alkoxysilane to form a grafted polymer, the polyorganosiloxane referred to should be understood as having one or more pendant hydroxyl groups.

DETAILED DESCRIPTION

Thermally conductive materials, also referred to as thermal interface materials, may be placed between two components (e.g., a chip and a heat sink) for heat removal (e.g., in an air cooled environment). In some cases, a silicone-based material may be used as a thermal interface material (e.g., for use in an air cooled environment). In the context of immersion cooling, mineral oil may represent an inexpensive immersion cooling fluid. However, mineral oil may be soluble in some silicone-based materials (e.g., a polydimethylsiloxane (PDMS) material), resulting in swelling of the thermal interface material. Swelling of the thermal interface material may reduce the efficiency of heat removal between the two components. As such, a silicone-based thermal interface material that provides satisfactory heat removal characteristics in an air cooled environment may provide unsatisfactory heat removal characteristics in an immersion cooling environment (e.g., where mineral oil is used as the cooling fluid).

To illustrate, the Hildebrand solubility parameter ($\delta$) (referred to herein as the "solubility parameter") of mineral oil is 7.09 $cal^{1/2}$ $cm^{-3/2}$, while the solubility parameter of PDMS is 7.3 $cal^{1/2}$ $cm^{-3/2}$. It is generally accepted that if the difference in solubility parameters between two materials is less than or equal to about 2 $cal^{1/2}$ $cm^{-3/2}$, then the two materials are considered to be soluble in one another. As the difference between the solubility parameters of mineral oil and PDMS is less than 2 $cal^{1/2}$ $cm^{-3/2}$, mineral oil is predicted to be soluble in PDMS. As such, the solubility of mineral oil in PDMS may result in swelling of a PDMS-based thermal interface material when immersed in mineral oil. Swelling of PDMS may cause a bond line between the two components to grow, with thermal performance decreasing as the bond line grows. As thermal resistance increases, the performance of the chip may decrease.

The present disclosure describes silicone-based materials that may be functionalized to shift the solubility parameter of the silicone-based material away from the solubility parameter of an immersion cooling fluid (e.g., mineral oil) in order to allow such materials to be used in an immersion cooled environment (as well as an air cooled environment). In a particular embodiment, a PDMS material may be functionalized in order to shift the solubility parameter of the PDMS material by at least two solubility parameter units (e.g., units of $cal^{1/2} cm^{-3/2}$) away from that of mineral oil. Functionalization of the PDMS material may reduce or eliminate swelling of the PDMS material when immersed in mineral oil. As such, the functionalized PDMS material of the present disclosure may be used as a thermal interface material in both an air cooled environment and an immersion cooling environment.

While the present disclosure describes examples of materials and processes for preparation of functionalized silicone-based thermal interface materials for use in mineral oil immersion cooling, it will be appreciated that alternative materials and/or processes may be used. For example, while mineral oil is described as an example of an immersion cooling fluid, other fluids may be used for immersion cooling. Thus, while materials and processes are described to shift the solubility parameter of a PDMS material by at least 2 solubility parameter units from the solubility parameter of mineral oil (e.g., from 7.09 $cal^{1/2} cm^{-3/2}$ to at least 9.09 $cal^{1/2} cm^{-3/2}$) in order to reduce mineral oil solubility in the PDMS material, it will be appreciated that similar techniques may be employed to shift the solubility parameter away from an alternative immersion cooling fluid. As another example, while PDMS is described as an example of a silicone-based material, it will be appreciated that alternative and/or additional silicone-based materials may be used. Thus, while materials and processes are described to shift the solubility parameter of PDMS (7.3 $cal^{1/2} cm^{-3/2}$) to about 2 solubility parameter units from the solubility parameter of mineral oil in order to reduce/prevent mineral oil solubility in PDMS, it will be appreciated that similar techniques may be employed to shift the solubility parameter of an alternative silicone-based material.

Further, while the present disclosure describes specific examples of propanol modification of PDMS (having a solubility parameter of 7.3 $cal^{1/2} cm^{-3/2}$) based on the solubility parameter of 1-propanol of 11.94 $cal^{1/2} cm^{-3/2}$, alternative and/or additional material(s), alternative and/or additional amount(s) of material(s), or a combination thereof may be used to form a functionalized PDMS material. It will be appreciated that the material(s)/amount(s) may be adjusted such that the functionalized PDMS material has a solubility parameter that is at least 2 solubility parameter units removed from that of mineral oil (7.09 $cal^{1/2} cm^{-3/2}$) in order to reduce/eliminate mineral oil solubility when the functionalized PDMS material is used as a thermal interface material in an immersion cooling environment.

Referring to FIG. 1, a chemical reaction diagram 100 illustrates the preparation of a functionalized silicone-based material (in protected form), according to an embodiment. In FIG. 1, three chemical reactions are illustrated. The first chemical reaction (shown at the top of FIG. 1) illustrates a protecting group being used to render a hydroxyl group of a brominated alcohol non-reactive. The second chemical reaction (shown at the middle of FIG. 1) illustrates the protected brominated alcohol being used to form a protected alcohol silane. The third chemical reaction (shown at the bottom of FIG. 1) illustrates the protected alcohol silane being used to form a functionalized silicone-based material (in protected form). As described further herein with respect to FIG. 2, the functionalized silicone-based material of FIG. 1 may be deprotected to form a functionalized silicone-based thermal interface material (e.g., for use in immersion cooling applications).

In the first chemical reaction illustrated in FIG. 1, a brominated alcohol (e.g., 3-bromo-1-propanol) is reacted with a protecting group (e.g., tert-Butyldimethylsilyl chloride (TBSCl)), with TBS acting as a protecting agent for oxygen (as shown by the replacement of hydrogen in the hydroxyl group of the brominated alcohol with TBS on the right side of the first chemical reaction diagram). A quantity of the protecting group that is reacted with the brominated alcohol may be sufficient to render a hydroxyl group of the brominated alcohol non-reactive.

Prophetic Example: Preparation of Protected 3-bromo-1-propanol

As a prophetic example, 3-bromo-1-propanol (3.00 g, 21.5 mmol), may be dissolved in 70 mL of dry tetrahydrofuran (THF). The solution may be cooled to about −78° C. under argon. N-Butyllithium in hexane (13.1 mL, 2.4 M, 31.5 mmHg) may be added (e.g., dropwise), and the reaction may be allowed to warm to room temperature over about 1 hour. tert-Butyldimethulsilyl chloride (TBSCl) (4.60 g, 30.0 mmol) may be added in 20 mL of dry THF. The resulting mixture may be stirred for about 30 minutes, followed by the addition of a catalytic amount of imidazole (0.1 g). The mixture may be stirred for about 12 hours, followed by dilution with 70 mL of saturated aqueous $NaHCO_3$ and extracted with ether (3×70 mL). The resulting ether extracts may be dried (e.g., using $Na_2SO_4$), filtered, and concentrated to afford the product.

In the second chemical reaction of FIG. 1, silane functionality is added to the protected brominated alcohol formed in the first chemical reaction. In the example of FIG. 1, an alkoxysilane (e.g., tetraethoxysilane, illustrated as "Si(OEt)$_4$" in FIG. 1) is chemically reacted with the protected brominated alcohol to form a protected alcohol silane. The right side of the chemical reaction diagram illustrates the addition of the silane functionality via replacement of the bromine group in the protected brominated alcohol with triethoxysilane (illustrated as "(OEt)$_3$Si" in FIG. 1).

Prophetic Example: Preparation of 3-(triethoxysilyl)propan-1-ol

As a prophetic example, 8,8-diethoxy-2,2,3,3-tetramethyl-4,9-dioxa-3,8-disila undecane may be prepared by slow addition of (3-bromopropoxy)(tert-butyl)dimethylsilane (7.56 g, 0.03 mol) to magnesium turnings (0.73 g, 0.03 mol) in THF under argon atmosphere. The solution may then be boiled for about 20 hours. Tetraethoxysilane (5 g, 0.024 mol) in THF may be added to the solution (e.g., dropwise). The solution may then be refluxed for about 15 hours. The resulting product may be purified by vacuum distillation.

In the third reaction illustrated in FIG. 1, a polyorganosiloxane (e.g., a hydroxyl-terminated PDMS) and the protected alcohol silane formed in the second chemical reaction are combined to form a mixture. The mixture is polymerized to form a grafted polyorganosiloxane then fully condensed. In the particular embodiment illustrated in FIG. 1, the protected alcohol silane may represent about 4 to 5 weight percent of the mixture. A weight percentage of the protected alcohol silane in the mixture may vary, with the amount of protected alcohol silane being adjusted in order to shift the solubility parameter by at least 2 solubility parameter units from that of mineral oil (e.g., to at least 9.09 $cal^{1/2}$ $cm^{-3/2}$ based on mineral oil's solubility parameter of 7.09 $cal^{1/2}$ $cm^{-3/2}$) in order to reduce/eliminate the solubility of mineral oil in the functionalized PDMS (after deprotection of oxygen to replace TBS with hydrogen to form pendant alcohol groups, as illustrated and further described herein with respect to FIG. 3).

To illustrate, while the solubility parameter of PDMS is 7.30 $cal^{1/2}$ $cm^{-3/2}$, and the solubility parameter of 1-propanol is 11.94 $cal^{1/2}$ $cm^{-3/2}$, it will be appreciated that the solubility parameter of the functionalized PDMS material may be greater than 7.30 $cal^{1/2}$ $cm^{-3/2}$ but less than 11.94 $cal^{1/2}$ $cm^{-3/2}$, depending on an amount of protected alcohol silane that is polymerized with the PDMS.

In a particular embodiment, an amount of protected alcohol silane that is polymerized with the hydroxyl-terminated PDMS may be sufficient to form (after deprotection) a functionalized PDMS thermal interface material having a solubility parameter of at least 9.09 $cal^{1/2}$ $cm^{-3/2}$ (e.g., for use in mineral oil immersion cooling). In some cases, the amount of protected alcohol silane that is polymerized with the hydroxyl-terminated PDMS may be sufficient to form (after deprotection) a functionalized PDMS thermal interface material having a solubility parameter in a range from 9.09 $cal^{1/2}$ $cm^{-3/2}$ to 11.94 $cal^{1/2}$ $cm^{-3/2}$, such as in a range from 9.09 $cal^{1/2}$ $cm^{-3/2}$ to 10.94 $cal^{1/2}$ $cm^{-3/2}$, in a range from 9.09 $cal^{1/2}$ $cm^{-3/2}$ to 9.94 $cal^{1/2}$ $cm^{-3/2}$, or in a range from 9.09 $cal^{1/2}$ $cm^{-3/2}$ to 9.44 $cal^{1/2}$ $cm^{-3/2}$.

It will be appreciated that, in cases where the immersion cooling fluid(s) includes alternative and/or additional fluids, similar adjustments may be made to the amount of protected alcohol silane that is polymerized with the PDMS in order to shift the solubility parameter of PDMS by at least 2 solubility parameter units from the solubility parameter of the alternative immersion cooling fluid(s). To illustrate, in the event that a mixture of mineral oil and another oil is used, the mixture may have a solubility parameter that is greater than 7.09 $cal^{1/2}$ $cm^{-3/2}$ (the solubility parameter of mineral oil) or that is less than 7.09 $cal^{1/2}$ $cm^{-3/2}$. As such, an amount of protected alcohol silane that is polymerized with PDMS may be adjusted based on the particular immersion cooling fluid (or fluids) in order to reduce/prevent immersion fluid solubility in the PDMS thermal interface material.

Prophetic Example: Preparation of 1-propanol Modified PDMS

As a prophetic example, a hydroxyl-terminated PDMS containing a pendent hydroxyl group from the polymer backbone (5.5 g) may be dissolved in 150 mL of ethanol at room temperature. The mixture may be placed in an ultrasonic homogenizer for about 5 minutes and then placed into a 500 mL three-neck round bottom flask with a mechanical stirrer in a 60° C. oil bath. 8,8-diethoxy-2,2,3,3-tetramethyl-4,9-dioxa-3,8-disila undecane (e.g., about 4-5 wt %) may then be added with dropwise acidic water (5 mL, pH=1, using acetic acid) under mechanical stirring. The reaction may be allowed to proceed for about 2 hours followed by purification to yield product. The resulting silicone may be fully condensed.

Thus, FIG. 1 illustrates an example of a process of preparing a functionalized silicone-based material (in protected form). In the example of FIG. 1, in order to graft an alcohol (e.g., 1-propanol) onto a PDMS polymer chain, a protecting group may be reacted with an alcohol (e.g., a brominated alcohol) to protect the oxygen of the hydroxyl group, and the protected brominated alcohol may be reacted with an alxoysilane to form a protected alcohol silane. The protected alcohol silane may then be polymerized with a silicone-based material (e.g., PDMS) to form a grafted material (in protected form) and fully condensed (not shown). As illustrated and further described herein with respect to FIG. 2, deprotection results in a 1-propanol modified PDMS material (e.g., for use as a silicone-based thermal interface material in an immersion cooling environment).

Figure 2:
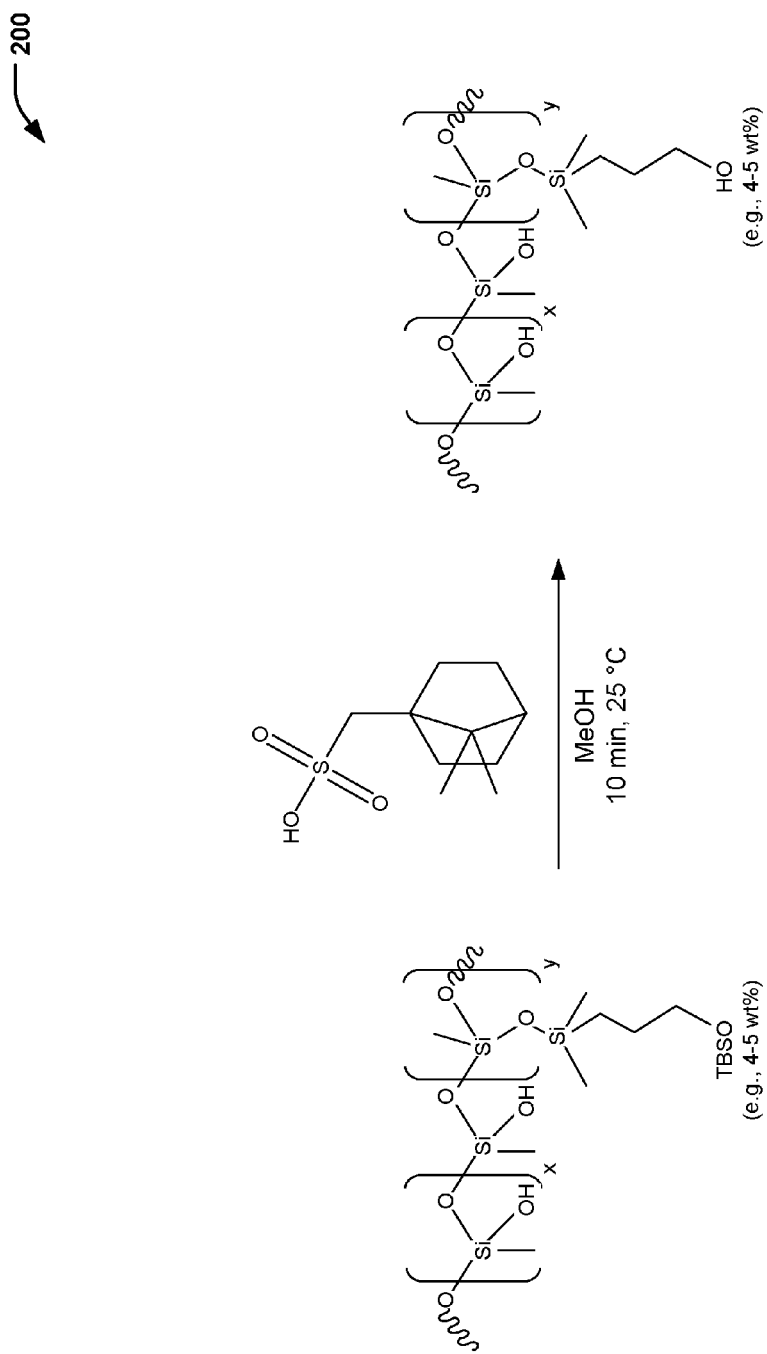
FIG. 2 is a chemical reaction diagram showing the deprotection of the protected silicone-based material of FIG. 1 to form a functionalized silicone-based thermal interface material, according to an embodiment.

Referring to FIG. 2, a chemical reaction diagram 200 illustrates the deprotection of the protected PDMS material of FIG. 1 to form a functionalized silicone-based thermal interface material (e.g., for immersion cooling applications), according to an embodiment. FIG. 2 illustrates that removal of the protecting group (e.g., TBS) results in a 1-propanol modified PDMS thermal interface material (that may be mixed with a thermally conductive material such as alumina, as further described herein).

In the chemical reaction illustrated in FIG. 2, the protecting group (e.g., TBS in this case) may be removed from the fully condensed PDMS material of FIG. 1. In the embodiment illustrated in FIG. 2, methanol (MeOH) and camphorsulfonic acid are used to remove the TBS protecting group, as shown on the right side of the chemical reaction diagram.

In a particular embodiment, the 1-propanol modified PDMS material of FIG. 2 may have a solubility parameter of at least 9.09 $cal^{1/2}$ $cm^{-3/2}$ (e.g., for use in mineral oil immersion cooling). In some cases, the 1-propanol modified PDMS material of FIG. 2 may have a solubility parameter in a range of 9.09 $cal^{1/2}$ $cm^{-3/2}$ to 11.94 $cal^{1/2}$ $cm^{-3/2}$, such as in a range of 9.09 $cal^{1/2}$ $cm^{-3/2}$ to 10.94 $cal^{1/2}$ $cm^{-3/2}$, in a range of 9.09 $cal^{1/2}$ $cm^{-3/2}$ to 9.94 $cal^{1/2}$ $cm^{-3/2}$, or in a range of 9.09 $cal^{1/2}$ $cm^{-3/2}$ to 9.44 $cal^{1/2}$ $cm^{-3/2}$.

While not shown in FIG. 2, the resulting 1-propanol modified PDMS material may then be mixed with a thermally conductive material (or multiple materials) for use as a silicone-based thermal interface material that may allow for hardware cooling in both an air environment as well as an immersive cooling environment. In a particular embodiment, a weight percentage of thermally conductive material (e.g., alumina) that is mixed with the 1-propanol modified PDMS material of FIG. 2 may be in a range of 0 to 85 weight percent, such as in a range of about 0 (e.g., 0.1) to 45 weight percent, in a range of 5 to 40 weight percent, in a range of 10 to 35 weight percent, in a range of 15 to 30 weight percent, or in a range of 20 to 25 weight percent.

Prophetic Example: Deprotection of 1-propanol Modified PDMS

As a prophetic example, protected 1-propanol modified PDMS may be placed into a round bottom flask with a mechanical stirrer. The PDMS may be dissolved in MeOH (150 mL). To the mixture, 1 g of camphorsulfonic acid (100 mol %) may be added at room temperature. After about 10 minutes, the reaction may be terminated, and the resulting product may be purified.

Thus, FIG. 2 illustrates an example of a process of forming a 1-propanol modified PDMS thermal interface material. By grafting a material having a higher solubility parameter (in this case 1-propanol, with a solubility parameter of 11.94 cal$^{1/2}$ cm$^{-3/2}$) than the PDMS material, the solubility parameter may be increased to reduce/prevent immersion cooling fluid solubility in the PDMS material. While FIG. 2 illustrates an example in which the 1-propanol modified portion of the PDMS material corresponds to about 4 to 5 weight percent of the polymer, it will be appreciated that alternative weight percentages may be used in order to adjust the solubility parameter (e.g., to at least 2 solubility parameter units (cal$^{1/2}$ cm$^{-3/2}$) away from that of mineral oil).

Figure 3:
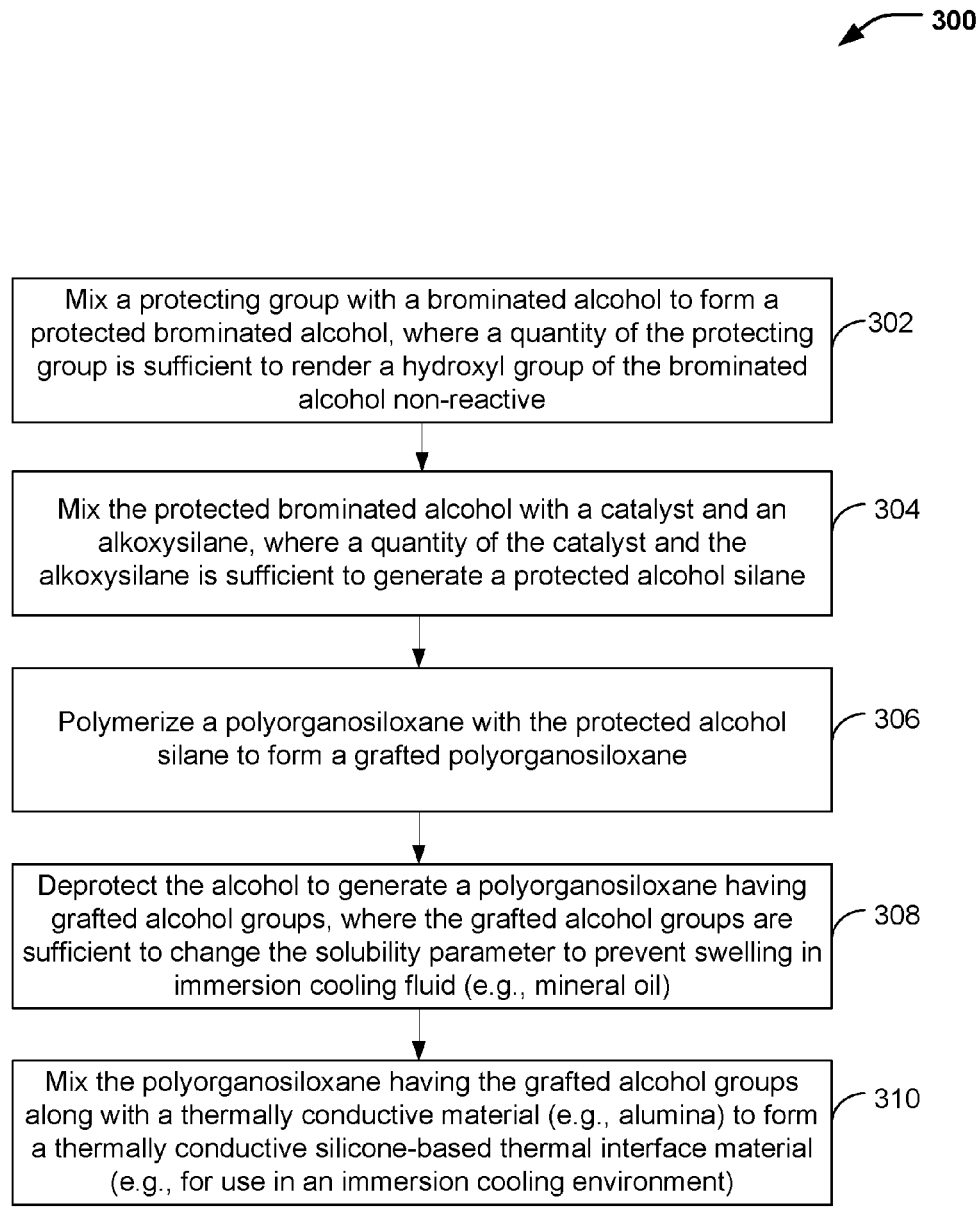
FIG. 3 is a flow diagram showing a particular embodiment of a process of preparing a functionalized silicone-based thermal interface material.

FIG. 3 is a flow diagram of a particular embodiment of a process 300 of preparing a functionalized silicone-based thermal interface material. In FIG. 3, a material having a solubility parameter that is different from a silicone-based material may be polymerized with the silicone-based material in order to shift the solubility parameter of the resulting functionalized silicone-based thermal interface material. Shifting the solubility parameter away from an immersion cooling fluid, such as mineral oil, may reduce/prevent solubility of the immersion cooling fluid in the silicone-based material. The solubility parameter adjustment may reduce/prevent heat transfer performance reduction that may be associated with swelling of a silicone-based thermal interface material that has a solubility parameter that is similar to that of the immersion cooling fluid(s).

The process 300 includes mixing a protecting group with an alcohol (e.g., a brominated alcohol), at 302. In the case of a brominated alcohol, the protecting group may react with the hydroxyl group(s) to form a protected brominated alcohol. A quantity of the protecting group that is mixed with the alcohol may be sufficient to render the hydroxyl group(s) of the alcohol non-reactive. For example, referring to the first chemical reaction illustrated in FIG. 1, a brominated alcohol (e.g., 3-bromo-1-propanol) is reacted with a protecting group (e.g., TBSCl), with TBS acting as a protecting agent for oxygen (as shown by the replacement of hydrogen in the hydroxyl group of the brominated alcohol with TBS on the right side of the first chemical reaction diagram).

The process 300 includes mixing the protected alcohol (e.g., a protected brominated alcohol) with a catalyst and an alkoxysilane to form a protected alcohol silane, at 304. A quantity of the catalyst and the alkoxysilane may be sufficient to generate a protected alcohol silane. For example, referring to the second chemical reaction illustrated in FIG. 1, an alkoxysilane (e.g., tetraethoxysilane) is chemically reacted with the protected brominated alcohol formed in the first chemical reaction to form the protected alcohol silane. The right side of the chemical reaction diagram illustrates the addition of the silane functionality via replacement of the bromine group in the protected brominated alcohol with triethoxysilane (illustrated as "(OEt)$_3$Si" in FIG. 1).

The process 300 includes polymerizing a polyorganosiloxane with the protected alcohol silane to form a grafted polyorganosiloxane (and fully condensing), at 306. For example, referring to the third chemical reaction diagram in FIG. 1, a polyorganosiloxane (e.g., a hydroxyl-terminated PDMS) and the protected alcohol silane formed in the second chemical reaction are polymerized to form the grafted polyorganosiloxane (in protected form) and then fully condensed (not shown).

The process 300 includes deprotecting the alcohol to generate a polyorganosiloxane having grafted alcohol groups, at 308. The grafted alcohol groups are sufficient to change the solubility parameter in order to reduce/prevent swelling in an immersion cooling fluid (e.g., mineral oil). For example, referring to FIG. 2, methanol and camphor-sulfonic acid may be used to remove the TBS protecting group, as shown in the right side of the chemical reaction diagram. As described further herein, the 1-propanol modified PDMS material of FIG. 2 may have a solubility parameter of at least 9.09 cal$^{1/2}$ cm$^{-3/2}$ (e.g., for use in mineral oil immersion cooling, where mineral oil has a solubility parameter of 7.09 cal$^{1/2}$ cm$^{-3/2}$).

In the particular embodiment illustrated in FIG. 3, the process 300 includes mixing the polyorganosiloxane having the grafted alcohol groups along with a thermally conductive material to form a thermally conductive silicone-based thermal interface material, at 310. The thermally conductive material may include alumina, and the resulting mixture may be used as a silicone-based thermal interface material in an immersion cooling environment.

To illustrate, the silicone-based thermal interface material may be disposed between a first component of an apparatus (e.g., a computing device) and a second component of the apparatus, where the first component represents a heat source. For example, the first component may include an integrated circuit, and the second component may include a heat sink. In this case, the computing device may represent a computing device that is designed to be operated in an air cooled environment. Shifting the solubility parameter of the silicone-based thermal interface material to not less than 9.09 cal$^{1/2}$ cm$^{-3/2}$ (e.g., at least 2 solubility parameter units from the solubility parameter of mineral oil) may allow the computing device to operate in not only an air cooled environment but also in an immersion cooled environment by reducing/preventing mineral oil from dissolving in the thermal interface material and degrading heat removal performance.

Thus, FIG. 3 illustrates an example of a process of preparing a functionalized silicone-based thermal interface material. In FIG. 3, a material having a solubility parameter that is different from a silicone-based material may be polymerized with the silicone-based material in order to shift the solubility parameter of the resulting functionalized silicone-based thermal interface material. Shifting the solubility parameter away from an immersion cooling fluid, such as mineral oil, may reduce/prevent solubility of the immersion cooling fluid in the silicone-based material.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein but is to be accorded the widest scope possible consistent with the principles and features as defined by the following claims.

The invention claimed is:

1. A process for the production of a silicone-based polymeric material, the process comprising:
   chemically reacting a protecting compound with a brominated alcohol to form a protected brominated alcohol;
   chemically reacting the protected brominated alcohol with magnesium to form an intermediate species, and reacting the intermediate species with an alkoxysilane to form a protected alcohol alkoxysilane;
   forming a mixture of the protected alcohol alkoxysilane and a hydroxyl-terminated polyorganosiloxane having one or more pendant hydroxyl groups;

polymerizing the mixture to form a grafted polyorganosiloxane having a protected alcohol; and deprotecting the protected alcohol of the grafted polyorganosiloxane to generate a silicone-based polymeric material having a solubility parameter that is not less than 9.09 $cal^{1/2}$ $cm^{-3/2}$.

2. The process of claim 1, wherein the brominated alcohol includes 3-bromo-1-propanol.

3. The process of claim 1, wherein the alkoxysilane includes tetraethoxysilane.

4. The process of claim 1, wherein the polyorganosiloxane includes a hydroxyl-terminated polydimethylsiloxane (PDMS) material.

5. The process of claim 4, wherein the PDMS material has a second solubility parameter of 7.3 $cal^{1/2}$ $cm^{-3/2}$, and wherein an amount of protected alcohol silane that is polymerized with the PDMS material is sufficient to shift the solubility parameter of the silicone-based polymeric material to within a range of 9.09 $cal^{1/2}$ $cm^{-3/2}$ to 11.94 $cal^{1/2}$ $cm^{-3/2}$ for use as an silicone-based thermal interface material in an immersion cooling environment where mineral oil having a solubility parameter of 7.09 $cal^{1/2}$ $cm^{-3/2}$ is used as an immersion cooling fluid.

\* \* \* \* \*